United States Patent [19]
Van de Velde

[11] Patent Number: 5,568,208
[45] Date of Patent: Oct. 22, 1996

[54] MODIFIED SCANNING LASER OPTHALMOSCOPE FOR PSYCHOPHYSICAL APPLICATIONS

[76] Inventor: Frans J. Van de Velde, 2 Hawthorne Pl. 15-O, Boston, Mass. 02114

[21] Appl. No.: 207,385

[22] Filed: Mar. 8, 1994

[51] Int. Cl.$^6$ ........................................ A61B 3/10
[52] U.S. Cl. ........................... 351/221; 351/205
[58] Field of Search ........................ 351/200, 205, 351/206, 208, 221; 354/62

[56] References Cited

U.S. PATENT DOCUMENTS

| | | | |
|---|---|---|---|
| 4,213,678 | 7/1980 | Pomerantzeff et al. | 351/206 |
| 5,308,919 | 5/1994 | Minnich | 351/221 |

OTHER PUBLICATIONS

Nasemann and Burk, Scanning Laser Ophthalmoscopy . . . ISBN 3-928036-01-7 Chapter 1 and 2, pp. 23 to 46 (1990).
Wyszecki and Stiles, Color Science: concepts and . . . ISBN 0-471-02106-7 Chapter 5.11 Stiles-Crawford effect pp. 424 to 429; Chapter 5.15.1/2/3 Maxwellian view, pp. 478-485 (1982).

Primary Examiner—William L. Sikes
Assistant Examiner—Huy Mai

[57] ABSTRACT

A modified scanning laser ophthalmoscope expands the range of clinical applications of the conventional scanning laser ophthalmoscope, being able of presenting the scanning laser raster with graphics to the retina and simultaneously allowing the observation of the anterior segment on the display monitor. The device, including a beamsplitter, infrared lightsource, scanning laser ophthalmoscope, CCD camera, and optical filters, determines unambiguously in real-time the entrance pupil of the Maxwellian view scanning laser ophthalmoscope. The location of the entrance pupil and stimulus position on the retina can be moved independently.

6 Claims, 2 Drawing Sheets

MODIFIED SCANNING LASER OPTHALMOSCOPE FOR PSYCHOPHYSICAL APPLICATIONS

BACKGROUND-CROSS REFERENCE TO RELATED APPLICATION

The invention uses the scanning laser ophthalmoscope proper of co-pending application, Ser. No. 08/178,777, filed 1994 Jan. 7.

1. Background-Field of Invention

This invention relates generally to instruments for examining the eye and specifically to an electro-optical ophthalmoscope for providing simultaneously a precise visual representative of the eye fundus, anterior eye segment, and eye functioning on a display monitor.

2. Background-Description of Prior Art

The ophthalmoscope is well known as an important aid for studying and examining the eye, and in particular, the fundus of the eye. As a result of great interest in preserving man's eyesight, ophthalmoscopes of various constructions have been built and used. The latest version of the ophthalmoscope, a scanning laser ophthalmoscope, is particularly appealing because of its unique capability of combining the visualization of the retina or eye fundus with certain psychophysical and electrophysiological testing procedures, used in studying the subjective or objective functioning of the visual pathways, from the retina to the brain cortex. With the scanning laser ophthalmoscope, a unique, precise correlation between retinal anatomy and function is established. Many different stimuli that are used in visual psychophysics, can be projected onto the fundus with the help of the scanning laser ophthalmoscope. Computer red overlay graphics are then used to display the stimulus characteristics such as size, location, and intensity on the fundus image in real-time. Detailed functional mapping of the fundus is thereby possible. Such functional mapping that is currently possible emulates classic Goldmann kinetic perimetry and automated static perimetry under light-adapted testing conditions. Until the invention, the scanning laser ophthalmoscope, has been limited to the examination of the posterior segment, excluding simultaneous imaging of both the retina, with presentation of psychophysical stimuli, and iris plane. Visualization of the anterior segment is however important because it allows an unambiguous observation of the entrance pupil of the Maxwellian view illumination used by the scanning laser ophthalmoscope. This is very significant since light entering near the center of the pupil is more efficient in eliciting a visual response than is light entering peripheral regions of the pupil. Not knowing the entrance pupil therefore precludes such testing as dark-adaptation, measuring dark-adapted thresholds and the Stiles-Crawford functions with the scanning laser ophthalmoscope.

Furthermore, eye movements and changes in the subject's fixation have hitherto limited the accuracy and ease of performing high resolution perimetry or microperimetry on the fundus. In practice, repeat trial and error presentation of one stimulus to one specific retinal location, using fiducial landmarks as a guide, can result in a waste of time, discomfort, decreased performance and limited information from the testing. The entrance pupil of the Maxwellian view is even more difficult to control manually since no reliable fiducial landmarks are available in the pupillary area.

OBJECTS AND ADVANTAGES

The principal objects of this invention are therefore to provide a modified scanning laser ophthalmoscope having the capability of presenting stimuli or graphics to the retina of one eye and to record simultaneously the entrance pupil coordinates of the Maxwellian view together with a view of the retina and stimulus or graphics overlay on a display monitor. The entrance pupil and stimulus location on the retina can be selected independently from each other and are subject to a passive, such as a bite-bar and trial-error-repeat stimulation, or active, such as fundus and pupil tracking, feedback mechanism to ensure their position regardless of eye movements or fixation shifts. With other words, it is possible now to take into account variations in visual function that are observed, not only when stimuli are imaged on different retinal areas, but also when stimuli enter the eye through different parts of the eye pupil on a monitor on the same very specific retinal area, displayed on a monitor. Several diverse objects and advantages of the device can be envisioned. In imaging, precise positioning of the entry pupil facilitates normal and off-axis dark-field viewing of the retina and brings an important variable in image-based reflectometry or densitometry measurements under control. As explained before, the entrance pupil of the Maxwellian view illumination is also a very important variable in functional testing of the eye, either subjective psychophysics or objective electrophysiology. Knowing its position during testing, allows measuring dark-adapted thresholds, Stiles-Crawford I and II effects, the Campbell effect, and dark-adaptation constants for specific areas of the fundus that can be visualized on the monitor. Active feedback tracking algorithms that document and stabilize the Maxwellian view and stimulus position on the retina are also the final step towards fully automated static microperimetry strategies. Stimulus presentations for example can be automatically repeated after the subject blinks or has repositioned in the chinrest.

It has been demonstrated that dark-adapted thresholds correlate with the amount of photopigment that is present in the retina. Dark-adaptation constants parallel the speed of replenishing of photopigment after bleaching. Stiles-Crawford functions reveal the general orientation and degree of alignment of the photoreceptors. Abnormalities in these parameters reveal damage to the retinal pigment epithelium-photoreceptor complex in the retina. This damage may be caused for example by a failure to maintain a critical oxygen gradient across the complex and as a result a reduced photopigment regeneration in Wald's cycle. It has been demonstrated that the abnormalities described above are relevant to visual functioning when macular disease, in particular the early stages of both types of age related macular degeneration, the leading cause of legal blindness in the United States, are present. Detailed functional retinal maps of the Stiles-Crawford functions, dark-adaptation and dark-adapted visual thresholds will very likely lead to insight in the physiopathology of the disease. They will prove to be useful in planning laser treatment indications, strategies, and follow-up. An example of such laser treatment could be the generation of oxygen windows through multiple mild chorioretinal burns. Further objects and advantages of the invention will become apparent from a consideration of the drawings and ensuing description.

DESCRIPTION OF THE DRAWINGS

Features and advantages of the invention will appear from the following description of preferred embodiments of the invention, taken together with the drawings in which.

REFERENCE NUMERALS IN DRAWINGS

Figure 1:
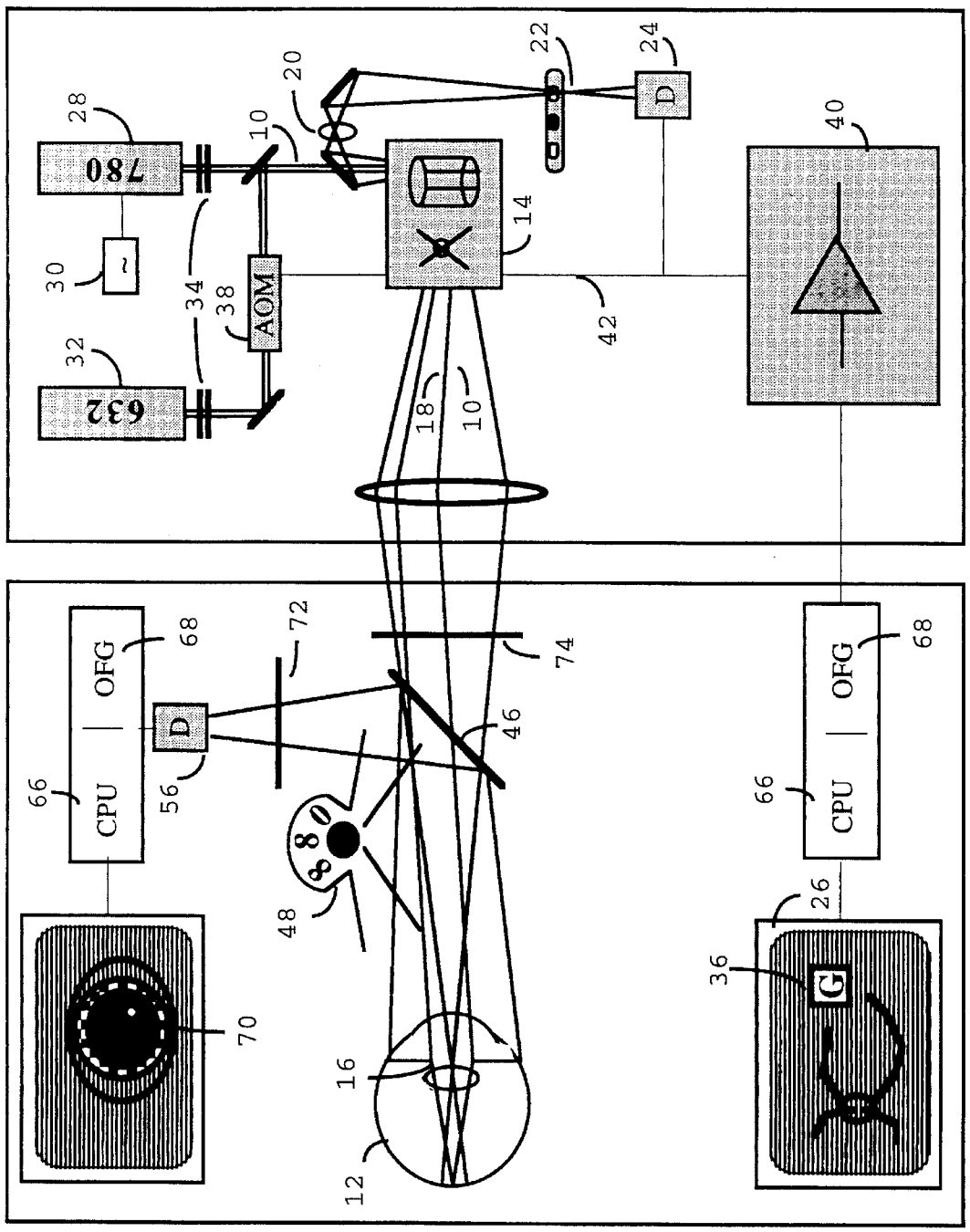
FIG. 1 is a diagrammatic representation, illustrating the general mode of operation of the modified scanning laser ophthalmoscope.

10 Prefocussed narrow Gaussian beam of laser light
12 Posterior pole of the fundus, retina
14 Scanners, including polygon and galvanometer
16 Optical entrance pupil of the Maxwellian view in the iris plane
18 Reflected and backscattered light from the eye
20 Beam separator
22 Pinhole at the retinal conjugate plane
24 Avalanche photodiode
26 Video display monitor
28 Diode infra-red 780 nm laser
30 Amplitude modulation of diode laser
32 He-Ne red 632 nm laser
34 Pair of adjustable linear polarizers
36 Graphics on the retina, visible as overlays
38 Acousto-optic modulator
40 Electronic circuitry of scanning laser ophthalmoscope
42 Distribution of common synchronization to different components
44 Encasement
46 Beamsplitter
48 Superluminescent 880 nm LED
50 Nose, cheeks and eyebrows
52 Cover of scanning laser ophthalmoscope
54 Slanted window of scanning laser ophthalmoscope with diaphragm
56 CCD videocamera with objective
58 Bite bar
60 Chinrest
62 Vertical movement mechanism using stepper motor
64 Horizontal two dimensional movement mechanism using stepper motors
66 486/33 mHz CPU with overlay frame grabber board
68 Overlay frame grabber board
70 Entrance pupil laser beam as overlay on image of anatomical pupil
72 Partial infrared barrier filter
74 Additional graded neutral density filter and diaphragm

DESCRIPTION AND OPERATION OF AN EMBODIMENT-FIG. 1,2

Figure 2:
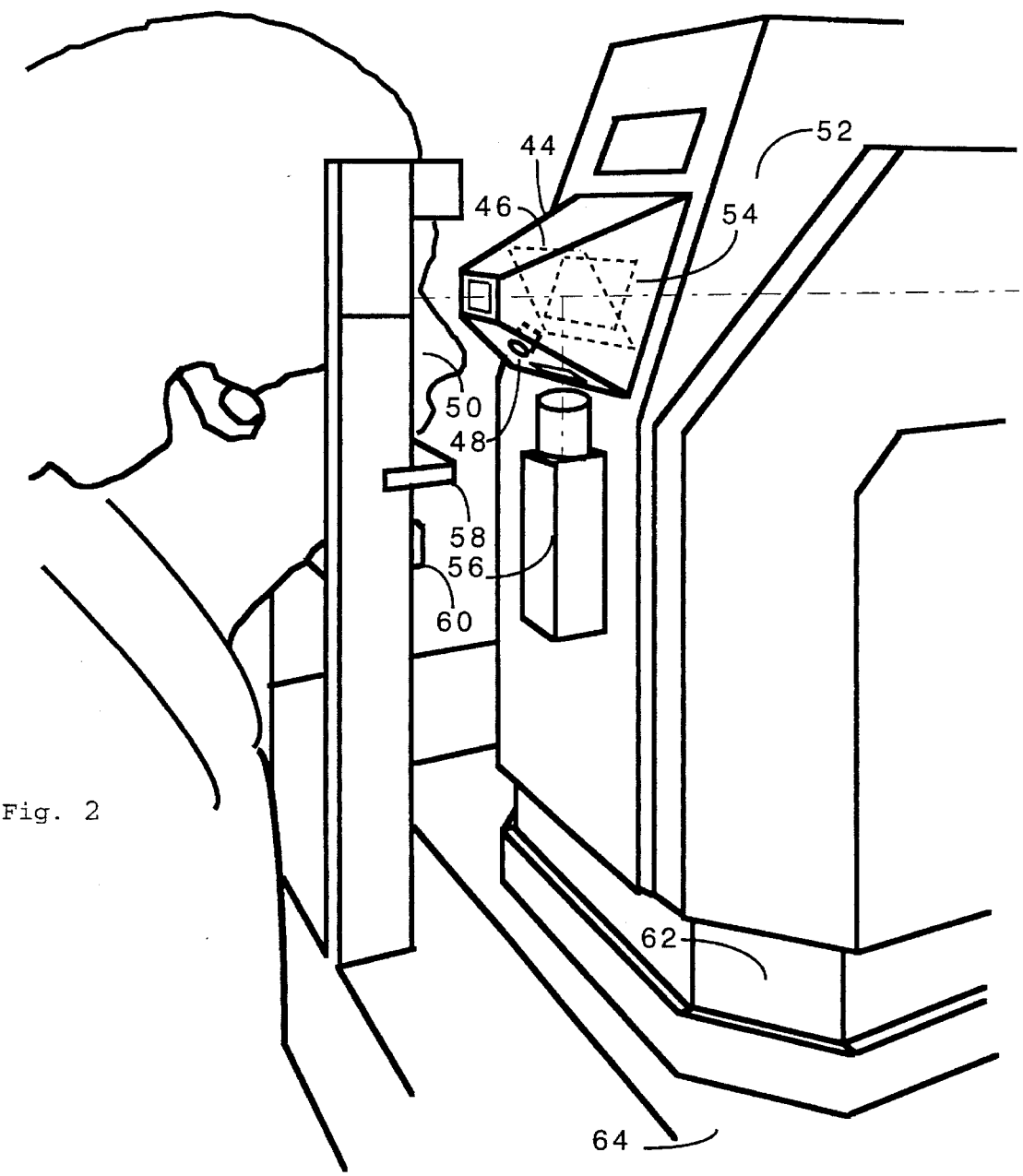
FIG. 2 is a perspective view of the modified scanning laser ophthalmoscope. The perspective view shows the spatial relationship between subject, scanning laser ophthalmoscope proper, and the electro-optical pathway including CCD camera, beamsplitter and anterior segment illumination.

A typical embodiment of the modified scanning laser ophthalmoscope is illustrated by FIG. 1 and 2. The principles of scanning laser ophthalmoscopy are described in detail in the prior art. Features relevant to the invention are further discussed.

THE SCANNING LASER OPHTHALMOSCOPE WITHIN THE MICROPERIMETER

A prefocussed narrow Gaussian beam of laser light 10, typically 12μ in diameter at the retinal plane, is scanned over the posterior pole of the eye 12 in a sawtooth manner with the help of scanning mirrors, currently a polygon and galvanometer 14. Both fast horizontal 15 KHz and slower vertical 60 Hz deflections of the flying laser spot are at standard video RS-170 rates with blanking intervals and create the rectangular laser beam raster that is seen by the subject. A Maxwellian view 16 is used in the illuminating portion of the scanning laser ophthalmoscope: the pivot point of the scanning laser beam is actually a tiny three dimensional volume optimally situated in the iris plane with an average waist of less than 1 mm. Typically a rectangular area of approximately 0.5 $cm^2$ on the retina is illuminated. This corresponds to a field of view of 40 degrees in diagonal or 32.7 degrees horizontally by 23.4 degrees vertically. The field of view can be changed with electronic or optical adjustments of the optical path. It is important to understand that the subject will not see a flying spot but rather a rectangle filled with thin horizontal stripes because of the temporal summation characteristics of the visual system. The reflected and backscattered light 18 of the eye, now filling the pupil, is descanned over the same mirrors, separated from the illuminating beam and passed through a pinhole 22 at the retinal conjugate plane before reaching a fast and sensitive avalanche photodiode 24. This confocal detection method is essential for obtaining high contrast specular pictures of the retina with infra-red illumination, by eliminating stray light at the pinhole. Non-confocal viewing modalities, also called dark-field, indirect or Tyndall imaging, are obtained by the insertion of a central stop instead of the pinhole 22 or off-axis illumination of the retina. The amount of light on the photodetector is translated into a voltage that modulates the intensity of an electron beam on the visual display cathode ray tube monitor 26. The electron beam moves synchronically with the scanning laser beam and a real-time video image of the fundus is likewise created on the display monitor. Two laser sources are aligned to illuminate the retina. The two lasers serve a different purpose. A high intensity diode infra-red 780 nm laser 28, electrically modulated and vertically polarized, is nearly invisible to the subject. It produces the retinal image on the display monitor. A superimposed low intensity He-Ne red 632.8 nm red laser 32, modulated with a pair of adjustable linear polarizers 34 and horizontally polarized, is visible to the eye. It is used to draw psychophysical stimuli 36 in the laser raster for projection onto the retina. These stimuli are created by amplitude modulation of the laserbeam at video rates as the red light passes through an acousto-optic modulator 38. The acousto-optic modulator is driven by a standard video source, usually a computer overlay frame grabber card that contains the graphics information, and is genlocked to the crystal clock of the electronic circuitry 40. Master timing signals are derived from the spinning polygon. It is important to understand the reason for using two different lasers. The scanning laser ophthalmoscope is very light efficient: about three orders of magnitude less light is necessary to visualize the fundus when compared with conventional ophthalmoscopes. However this light is still orders of magnitude the amount used for typical psychophysical testing. The problem is solved by using a 780 nm laser with sufficiently high output and for which the silicon detector of the scanning laser ophthalmoscope, but not the eye, is most sensitive, in combination with a low intensity 632 nm laser, for which the human eye is sensitive but insufficient for visualizing the fundus. This explains also why the stimuli which are perceived by the subject are usually not visible in the retinal picture, unless very bright. The exact position and characteristics of the stimuli can however be shown in real-time on the retinal image with the help of computer overlays as all image video out of the scanning laser ophthalmoscope, scanners, and graphics video into the acousto-optic modulator are synchronized to the same crystal clock 42. The scanning laser ophthalmoscope preferably uses achromatic refracting surfaces, such as mirrors and a polygon instead of lenses and acousto-optic deflectors, to prevent chromatic aberrations when combining two different wavelengths. Specific infra-red light retinal scatter and penetration, absorption, and reflection characteristics combine in a very complex fashion with the directional selectivity of light input, output and prefocussing of the laserbeam to visualize early and subtle changes in the photoreceptor—retinal pigment epithelium complex. These changes are hardly visible at times with conventional illumination techniques. The above mentioned variables, some of which are wavelength specific, together with video gain level, laser intensity, DC coupling within the monitor, and degree of pinhole or central stop determine the image appearance. High quality imaging is a prerequisite for Fundus related psychophysical testing. The scanning laser ophthalmoscope used in the modified scanning laser ophthalmoscope allows real-time and precise control of all the variables mentioned in this paragraph.

LASERSOURCES AND MODULATION OPTIONS

The diode 780 nm laser 28 can be replaced by a diode laser of longer wavelength, for example 904 nm. For every 10 nm increase in wavelength of the diode laser beyond 670 nm, the efficiency for stimulating the retina will be reduced to one half. This is useful in making the infra-red background illumination for visualizing the retina on the display monitor even less visible to the subject. Surface-emitting quantum-well laser diodes are of increasing interest, and offer the advantages of high packing densities on a wafer scale. An array of up to a million tiny individually modulated cylindrical $In_{0.2}Ga_{0.8}As$ surface-emitting quantum-well laser diodes with lasing wavelengths in the vicinity of 970 nm and shorter can substitute the traditional laser sources and scanners of a scanning laser ophthalmoscope. This will render the device more compact, less noisy, and less susceptible to mechanical wear and tear.

The 632.8 nm He-Ne laser 32 has been incorporated in the scanning laser ophthalmoscope because of its compact and sturdy design. It is however also the wavelength of choice for generating graphics and stimuli. Reasons for this preference are the maximal transmittance and minimal scatter within the transparent media of the eye, a minimal interference with the xanthophyll and hemoglobin pigments, and a monophasic cone response when compared with shorter visible wavelengths such as 488–514 nm blue/green argon. These advantages persist if a longer visible wavelength were chosen, e.g. a diode laser at 650 nm. In traditional Goldmann and automated perimeters, stimuli and background illumination are provided by different optical pathways, the lightsource however being the same. The advantages of this configuration are twofold. First, the background and stimulus fluctuate in the same amount as the lightsource is varying in intensity. Second, additional separate modulation of background and stimulus is possible with a neutral density filter and thereby a minimal or zero background with a maximum stimulus as permitted by the light source, is possible. Unlike the Goldmann and automated perimeters, stimuli and background illumination are always provided by the same optical path and light source in the scanning laser ophthalmoscope and cannot be further modulated with e.g. a separate neutral density filter for each channel. A truly zero background is not possible with either electrical amplitude modulation or acousto-optic modulation and the ratio between stimulus and background has a maximum limit. For acousto-optic modulation, the theoretical limit is 700, 300 is the practical and desired limit but very often only 100 is obtained. Incorporating the 650 nm diode laser can expand the dynamic range of stimulus to background illumination intensity by combining in parallel the electrical high-frequency amplitude modulation of the diode with the acousto-optic modulation described before. For this purpose the blue and red output of the overlay frame grabber board are used. The circuitry is easily constructed by s/he who is skilled in the art of electronics.

The measurement of dark-adapted thresholds, dark-adaptation and Stiles-Crawford functions require a minimal background and sufficiently intense maximum stimulus. A dynamic range of maximum stimulus intensity to background intensity of 2.5 log units is acceptable. As mentioned before, the acousto-optic modulator is driven by a standard video source, a computer overlay frame grabber card that contains the graphics information, and is genlocked to the crystal clock of the electronic circuitry. A typical example of such a video card is the FG 100-AT or more recently introduced, the OFG card, both available from Imaging Technology Inc., Bedford Mass. The OFG card is also the essential hardware for alignment and tracking of the pupil or fundus landmarks as described below. Two OFG cards, which are I/O mapped can reside in one CPU, typically equipped with a Intel 486/33-66 MHz microprocessor. The OFG board has to provide three basic functions for realizing the different psychophysical testing and imaging procedures with the scanning laser ophthalmoscope: generation of 8 bits graphics, frame grabbing and display of overlays. The different testing algorithms are constructed from an appropriate sequence of software routines by s/he who is skilled in the programming art. The library of basic software routines is, as usual, provided by the board manufacturer. Specific bitlevels of the graphics board, out of 256 possibilities, are combined with appropriate neutral density filter settings placed in various positions for approximate and fine tuning of laser light intensities. Using a combined neutral-density & beam modulation technique, we can obtain a uniform 0.1 log U intensity scale. This scale is often used in psychophysics. Individual bitlevels are translated into corresponding intensity levels by converting each bitlevel to an analog voltage with the D/A of the graphics board. This output voltage is then amplified and off-set by the AOM driver electronic circuit to obtain suitable voltages for modulating the amplitude of a radio-frequency carrier signal. The piezo-electric transducer of the acousto-optic-modulator is driven by this signal. Acoustic standing waves are created by the piezo-electric transducer. The atoms of the crystal then behave as a diffraction grating for the transversing laser beam. The amount of light passing through the diffraction grating as a first-order beam at the Bragg angle, defined by the frequency of the radio signal, is directly proportional to the amplitude of the radio-frequency signal. The time required for the AOM to adjust the intensity after changing bitlevels is called the AOM delay. The delay has to be accounted for in calibrating the overlay graphics. Inherent fluctuations in the electronics of D/A converter, AOM driver, and laser output will not affect the ratio of light intensities corresponding to any two bitlevels. Short term and long term variations of individual bitlevel intensities exist. Short term fluctuations are irrelevant for psychophysics since they are usually smaller than the psychophysical uncertainty and long term variations are neutralized with the help of a radiometer. Minimal spatial variations of light intensity also exist within the laser beam raster. They are neutralized with either software or a graded neutral density filter. Also a variability in local laser raster geometry has to be taken into account. A pincushion or trapezoid deformity of the near rectangular raster is caused by the internal optical configuration of the scanning laser ophthalmoscope. External angular dimensions of graphics are determined with the arctan formula. On the retina, equivalent linear distances are calculated using the standard observer's eye of LeGrand with an effective optical radius of 16.7 mm. 300µ on the retina equals 60 external minutes of arc. In practice, an uncertainty of about 10% in absolute size is expected because of the metric nonlinearities described and the variability in individual eye optics.

In summary, The laser raster itself is a very unusual for presenting graphics to the retina, graphics are presented in multiples of 33 ms, the time interval to draw one complete video frame on the retina. Each video frame consists of two interlaced video fields of 16.7 ms and 256 lines, the video fields may overlap during eye movements. Within each video field the graphics is composed of discrete pixels and every pixel is illuminated with a Gaussian beam profile in Maxwellian view for only 77 nanoseconds each. This is in sharp constrast with the smooth delivery of photons to the retina in conventional Ganzfeld, Newtonian illumination of standard perimeters. However the same number of photons arrive on the retina in both illumination systems, but with a completely different spatial and temporal distribution. Under physiologic testing conditions, it has been demonstrated that the laws of Bloch, Bunsen-Roscoe, Ricco, Weber-Fechner, Rose-DeVries, and the power law of psychophysics are applicable and equivalent in both illumination systems.

EXTERNAL APPEARANCE OF THE MODIFIED SCANNING LASER OPHTHALMOSCOPIC

The configuration of FIG. 2 is for use with the Rodenstock Scanning Laser Ophthalmoscope 101 or 102 (Munich, Germany). This configuration is readily adapted for other embodiments of the scanning laser ophthalmoscope by s/he who is skilled in the art. The principal new optical components of the modified scanning laser ophthalmoscope are contained in a moulded and closed encasement 44 for dust protection. These components include the beamsplitter 46, optical filters, and illumination source 48 for the anterior segment. The encasement is painted matt black on the inside to minimize unwanted scatter. It is tapered and provides as much sparing as possible for the bodily parts such as the nose, cheeks, and eyebrows of the subject 50 and has three optical apertures. The outside finishing matches that of the scanning laser ophthalmoscope 52 to which it is fitted tightly as a clip-on, easy to remove if necessary. All three apertures are protected by anti-reflection coated glass, centered on the optical axis, and may contain an optical filter as specified below. The aperture that is closest to the scanning laser ophthalmoscope measures about 5 by 5 cm, and is parallel with the slanted window of the scanning laser ophthalmoscope 54 at 15.6 degrees. This is helpful to eliminate unwanted reflections. The front aperture, about 1.5 by 1.5 cm, is facing the subject's eye, vertically, at a comfortable distance as to avoid touching the eyelashes. The third aperture, 2 by 2 cm, is superior or inferior, slanted, and faces a CCD monochrome videocamera with objective 56, which is firmly attached to the scanning laser ophthalmoscope. An appropriate objective would be the 25 mm 1.4 C mount Cosmicar lens from Asahi Precisicn Co., LTD., Japan with the 5 mm extension tube. An appropriate CCD videocamera would be the Sony XC-75 equipped with a ½ inch size interline-transfer CCD. The IR blocking filter has been removed from the camera and replaced by a dummy glass. The CCD camera can be easily removed and is in a fixed position relative to the encasement, even if the scanning laser ophthalmoscope moves. The axis of the CCD camera is vertical and coincides with the optical axis. An adjustable bite-bar 58 is attached to the movable chinrest 60 of the instrument. The scanning laser ophthalmoscope with the attachments described can move vertically with the help of a software controlled stepper motor 62. Two other stepper motors realize the horizontal movements of the scanning laser ophthalmoscope on a platform 64. A computer, equipped with one or two OFG cards, mouse, and keyboard control is provided 66, 68. One TV monitor displays the eye fundus with graphics overlay using the scanning laser ophthalmoscope. Another TV monitor or channel displays the anterior segment of the eye focussed on the iris with the CCD camera 70. It provides the exact position of the optical entrance pupil of the scanning laser ophthalmoscope as an overlay. The monitors, luminous control buttons, and reading light for the examiner are optically isolated from the subject. The only light reaching the subject is coming from the reduced-in-size anterior window of the scanning laser ophthalmoscope. This reduction is size is provided by a simple black diaphragm. It reduces unwanted light from within the scanning laser ophthalmoscope, unmodulated parts of the laser raster, and the horizontal edges of the video-fields that are produced by the horizontal scanning. These edges often have a higher irradiance because of the inertia in the scanning galvanometer mirror.

OPTICAL PATHWAYS IN THE MODIFIED SCANNING LASER OPHTHALMOSCOPE

With a modification and extension of the scanning laser ophthalmoscope optics it is possible to [1] visualize the posterior pole, retina or fundus of one eye in detail; [2] to project graphics, for example a 8 by 8 pixel square that is brighter than the background in Maxwellian view onto the retina; [3] simultaneously view the anterior segment of the eye on the same or different monitor, focussed on the iris plane and unambiguously demonstrating with the help of overlays the exact position of the laser beam in Maxwellian view used to draw the background and stimulus onto the retina; [4] both observations do not interfere with each other, the quality of the retinal image does not imply a lower quality of the iris image and the observation of the iris does not interfere with the purpose of psychophysical testing, for example by introducing a bright background; and [5] it is possible to independently of each other move the stimulus or graphics on the retina to any desired position and simultaneously, at will, move the scanning laser ophthalmoscope and entrance pupil of the laser beam within the anatomical pupil of the iris. Thereby the point of entry in the pupillary plane can be a variable in psychophysical testing where the stimulus location is kept constant and also it is possible to keep the entrance pupil fixed while moving the stimulus position on the retina.

In general, this is realized by [1] introducing a beamsplitter to provide two optical paths, one for the scanning laser ophthalmoscope proper and the second for visualizing the anterior segment of the eye; [2] The introduction of a separate illumination source for the anterior segment with appropriate filters to block unwanted light from reaching the CCD camera. [3] Active or passive stabilization of the stimulus on the retinal image, and entrance pupil of the Maxwellian view system. [4] The use of overlays with an appropriate graphics and videocard for demonstrating the exact position of the stimulus on the retina, and the exact position of the laserbeam in the anatomical pupil, these parts of the laserbee being used to create the background and stimulus visible to the subject. [5] The ability to move, manually or with the help of stepper motors the scanning laser ophthalmoscope relative to the subject, and the stimulus position on the retina with the help of the mouse or computer program.

Movement of the scanning laser ophthalmoscope in a frontal plane will cause the rays of the incident laser beam to use a different portion of the entrance pupil. This should not cause a shift in the position of the retinal image because the movement will displace the scanning laser beam rays in parallel and parallel rays will be focussed on the same spot. This same spot will however be illuminated in an oblique fashion and therefore a Tyndall phenomenon can be observed on the monitor, equivalent to the classic dark field microscopy. This is somewhat similar to the use of a central stop instead of a pinhole at the retinal conjugate plane.

The separate illumination source for the anterior segment can be a superluminescent light emitting diode LED, a close relative of the laser IR diode. The SY-IR53L is a Gallium Aluminium Arsenide super-high output infrared emitting diode in a T-1¾ package. It produces noncoherent, nonpolarized IR energy at 880 nm. 880 nm produces negligible interference with the psychophysical testing. The dispersion angle at half power point is 20 degrees. This is important to insure a fairly homogeneous illumination of the anterior segment from a short distance. The forward voltage is typically 1.3 V, power dissipation is 20 mA. Therefore a rechargeable NiCd battery pack is ideal to provide several hours of uninterrupted service. The radiant power output is at least 3.4 mW/sq.cm, enough to illuminate the entire anterior segment with a single diode. The small package allows a flexible montage of the diode in the encasement. The illumination of the anterior segment and anatomical pupil does not interfere with the fundus imaging. The wide angle distribution of the light, angulation of the diode, and a partial IR barrier filter 72 with manual control of the diaphragm in the objective reduce the interference from a first Purkinje image of both infrared lightsources. In particular the IR barrier filter removes most of the convergent 780 nm light during the testing procedure. An example is the Kodak Wratten gelatin filter 87C with no transmittance for 632.8 nm, 0.5% for 780 nm and more than 90% for 880 nm. Another example is the Kodak Wratten gelatin filter 87 with no transmittance for 632.8 nm, 30% transmittance for 780 nm and more than 90% transmittance for 880 nm. Two or more copies of this filter can be in series. This filter is only removed during calibration of the instrument when it becomes necessary to align the pivot area of the Maxwellian beam of 632.8 nm with an overlay on a piece of paper. This calibration is usually very steady since the beamsplitter, CCD camera and scanning laser ophthalmoscope are fixed relative to each other. The CCD camera is optimally sensitive for IR illumination. The crisp image of the anterior segment with the iris and pupil serve as the fiducial landmark for the manual or automated localization of the entrance pupil of the scanning laser ophthalmoscope. It should be stressed that the pivot point of 632.8 nm does not always correspond with the pivot point of 780 nm, and lightscatter will make the pivot point area look much larger than it is in reality, especially if higher energies are used.

Only a specific portion of the 632.8 nm beam is used for creating the stimulus and will therefore determine the true point of entry of the laserbeam. This may be different from the average position of the total beam. In practice it can be useful to distinguish the 4 quadrants of the pivot area. Further subdivision is not practical since the entrance beam has a very complex shape and the psychophysical test results have a relatively large margin of variability, exceeding the gain in accuracy from subdividing the entrance beam.

In general, the beamsplitter should favor transmission of 632.8 nm and 780 nm. Especially the transmission of 780 nm is critical for obtaining good fundus images. As discussed before the 780 nm can be replaced with a diode laser source of longer wavelength. The choice of the dielectric coatings for the beamsplitter 46 depends on the wavelengths used, their polarization status, and the angle of incidence of the laserlight. The ideal beamsplitter is nearly non-absorbing and as such the reflectance will be independent of the angle of incidence of the laserlight. The beamsplitter 46 consists of a single plane-parallel glassplate, 5 by 5 cm, with a partially reflecting low absorption dielectric coating on one side. The other side has an antireflection coating optimized for the angle of incidence of 45 degrees. This will prevent ghost images appearing on the video display monitor. A sample coating is HEBBAR™ (Melles-Griot, Irvine, Calif.). Some beamsplitters are highly polarization sensitive. In a particular scanning laser ophthalmoscope, the infra-red laser has vertical polarization of the E vector, p-plane with regard to the beamsplitter 46. The He-Ne laser has horizontal polarization of the E vector, s-plane with regard to the beamsplitter 46. Often ideal transmission-reflection characteristics can not be realized for all wavelengths involved. The most optimal coating permits a maximum of 780 nm to transmit, a maximum of 632.8 nm to transmit, and most of the 880 nm to reflect. The Melles-Griot, Irvine, Calif. #BTF 001 passes about 50% of the s-polarized 632.8 nm He-Ne light, more than 90% of the p-polarized 780 nm diode IR, and reflects about 20% of the 880 nm mixed polarization IR LED. Two options exist for equalizing within the laser raster the distribution of irradiant power of 632.8 nm light. As explained before, small differences in intensity are proper to the scanning laser ophthalmoscope for various reasons. The acousto-optic modulator can adjust intensities according to the location where stimuli are presented or the differences in irradiance can be neutralized with a custom build graded neutral density filter 74.

The insertion of an optical filter 74 and beamsplitter 46 in the optical pathway reduces the power of the 780 nm laserlight that illuminates the retina and additionally reduces the amount of light collected by the photodetector from the retina. It is reasonable to use a laser source that is more powerful. This source is already available in the scanning laser ophthalmoscope for indocyanin green angiography and is easily adapted for use with the modified scanning laser ophthalmoscope.

FUNDUS AND PUPIL TRACKING WITH THE MODIFIED SCANNING LASER OPHTHALMOSCOPE

As mentioned before, the entrance pupil and stimulus location on the retina can be selected independently from each other and are subject to a passive or active feedback mechanism to ensure their position regardless of eye movements or fixation shifts. The passive mechanisms include a bite-bar 58 and chinrest 60 to maintain the eye position. A simple trial-error-repeat strategy is used for presenting a stimulus to one specific retinal location under visual feedback control. Typically the pivot area is focussed on the iris using 632.8 nm light, prior to testing. The distance between iris and scanning laser ophthalmoscope is then maintained throughout the testing procedure in a passive fashion.

The active mechanisms make use of digital image processing techniques for pupil and fundus tracking. A second OFG board 68 within the same 486/33 mHz can perform these tasks using for example a technique called two-dimensional normalized gray-scale correlation. Such software is provided by Imaging Technology, Inc, Bedford, Mass. A 7 degree rotational tolerance and 120 ms search time are acceptable for the rather liberal requirements in clinical testing procedures. For pupil tracking the reference picture is the anterior segment, for retina tracking it is the fundus image. Feedback regarding eye movements and fixation shifts can be used to adjust the stepper motors 62, 64 or the psychophysical test algorithm. Typically the anterior segment image is either up-down or right-left reversed. It is possible to multiplex both video coming from the scanning laser ophthalmoscope and CCD camera. Therefore one computer with one boards is sufficient.

SUMMARY, RAMIFICATIONS, AND SCOPE

The modified scanning laser ophthalmoscope is an electro-optical device that broadens the range of clinical applications of the conventional scanning laser ophthalmoscope. With the device it is possible to visualize simultaneously the anterior segment of the eye with the exact position of the scanning laser beam, in Maxwellian view, and the posterior segment of the eye, the retina with graphics. Both observations are independent and do not influence each other in any adverse way. The observations occur in real-time. Small areas on the retina can be studied unambiguously with the scanning laser ophthalmoscope using tests that require knowledge of the position of the entrance pupil. In imaging, precise positioning of the entry pupil facilitates normal and off-axis dark-field viewing of the retina and allows measuring dark-adapted thresholds, Stiles-Crawford I and II effects, the Campbell effect, and dark-adaptation constants for specific areas of the fundus that can be visualized on the monitor. Active feedback tracking algorithms are the final step towards truly automated static microperimetry strategies. Although the description above contains many specificities, these should not be construed as limiting the scope of the invention but as merely providing illustrations of some of the presently preferred embodiments of this invention. Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the examples given.

I claim:

1. A scanning laser ophthalmoscope with Maxwellian view control for imaging and psychophysics, comprising of:

(A) a scanning laser ophthalmoscope, using Maxwellian view illumination and having (1) illuminating means including at least one wavelength in the visible range and a wavelength in the infra-red range of the spectrum for visualizing the posterior segment or retina of the eye and psychophysical testing, said scanning laser ophthalmoscope also provided with (2) a modulating means for creating psychophysical stimuli in the visible laser raster of said scanning laser ophthalmoscope and (3) an electronic means for generating video and common synchronization signal;

(B) a second imaging device, using free Newtonian viewing, for visualizing the anterior segment of the eye and the reflection or backscatter of the coincident illuminating means of said scanning laser ophthalmoscope in the pupillary area and on the iris, simultaneously with the observation of the posterior segment of the eye with said scanning laser ophthalmoscope, said imaging device allowing this simultaneous viewing of both the anterior and posterior segment of the eye without affecting adversely the quality of the retinal image, and said imaging device having focusing means to document the extent and location of the Maxwellian view in the pupillary area using the anterior segment as a fiducial landmark;

(C) an imaging board with means for overlay graphics, CPU and monitor, for controlling modulating means in said scanning laser ophthalmoscope and displaying simultaneously the extent and precise location of the Maxwellian view in the pupillary area of the anterior segment together with an image of the retina and the characteristics of any psychophysical stimulus projected onto the retina using modulating means of said scanning laser ophthalmoscope;

whereby the simultaneous availability of both images of the anterior and posterior segment of the eye enable said scanning laser ophthalmoscope to freely move, maintain and adjust for focusing the Maxwellian view illumination in the pupillary area of the eye, simultaneously document the unambiguous position of this Maxwellian view on an image of the pupillary area of the eye and simultaneously document the retinal image with the position of any stimulus of which the location can be selected independently from the selection of a location in the pupillary area for the Maxwellian view illumination, thereby allowing to measure the Stiles-Crawford effect on imaging and psychophysics for selected Maxwellian view illumination and selected retinal area.

2. The scanning laser ophthalmoscope with Maxwellian view control according to claim 1 further including the improvement of a beamsplitter for changing the optical path from the anterior segment of the eye to said imaging device, said beamsplitter introduced in such manner as to allow said scanning laser ophthalmoscope to retain optimal frontal position with regard to the eye and said beamsplitter not affecting the quality of the retinal image and anterior segment;

whereby combination of said scanning laser ophthalmoscope with said imaging device and with said beamsplitter optimizes the viewing of the anterior segment of the eye by allowing less restrictions imposed on size and position of said imaging device and by providing a frontal viewing of the pupillary area, thereby facilitating and making more precise the moving, maintaining and documenting the size and location of the Maxwellian view illumination of said scanning laser ophthalmoscope ophthalmoscope in the pupillary area.

3. The scanning laser ophthalmoscope with Maxwellian view control according to claim 1 further comprising second infra-red light illuminating means, using a third wavelength, for the anterior segment of the eye, said second infra-red light illuminating means adjusted in intensity, properly oriented and using such wavelength that no adverse effect is created for observing the retina and projecting psychophysical stimuli with said scanning laser ophthalmoscope;

whereby an improved visualization of fiducial landmarks is obtained around the pupillary area in the anterior segment for the localization of the reflection and backscatter of illuminating means of said scanning laser ophthalmoscope in the pupillary area.

4. A method for controlling the Maxwellian view illumination of a scanning laser ophthalmoscope during imaging and psychophysics comprising the steps of:

(A) visualizing the posterior segment or retina of the eye and psychophysical testing with a scanning laser ophthalmoscope, using Maxwellian view illumination with illuminating means comprising at least one wavelength in the visible range and a wavelength in the infra-red range of the spectrum, said scanning laser ophthalmoscope also providing psychophysical stimuli in the visible laser raster of said scanning laser ophthalmoscope with a modulating means and providing common synchronization of all video signals using electronic means;

(B) visualizing the anterior segment of the eye with the reflection and backscatter of the coincident illuminating means of said scanning laser ophthalmoscope using a second imaging device and free Newtonian viewing, simultaneously with the observation of the posterior segment of the eye with said scanning laser ophthalmoscope, said imaging device permitting simultaneous viewing of both the anterior and posterior segment of the eye without restricting the visualization of the retinal image, and said imaging device having a focusing means for documenting the extent and location of the Maxwellian view illumination in the pupillary area using the anterior segment as a fiducial landmark;

(C) controlling modulating means in said scanning laser ophthalmoscope with an imaging board permitting overlay graphics, CPU and monitor, and displaying simultaneously the extent and location of the Maxwellian view in the pupillary area of the anterior segment together with an image of the retina and the overlay of any psychophysical stimulus projected onto the retina using modulating means of said scanning laser ophthalmoscope;

whereby the availability of both images of the anterior and posterior segment of the eye allows said scanning laser ophthalmoscope to freely move, maintain and adjust for focusing the Maxwellian view illumination in the pupillary area of the eye, simultaneously document the unambiguous position of this Maxwellian view on an image of the pupillary area of the eye and simultaneously document the retinal image with the overlay of any stimulus of which the location can be selected independently from the selection of a location of the Maxwellian view illumination, thereby allowing to demonstrate the Stiles-Crawford effect on imaging and psychophysics for combination of selected Maxwellian view illumination and selected retinal area.

5. The method for controlling the Maxwellian view illumination of a scanning laser ophthalmoscope according to claim 4 further including the improvement of the use of a beamsplitter for changing the optical path from the anterior segment of the eye to said imaging device, said beamsplitter introduced in such manner as to allow said scanning laser ophthalmoscope to retain optimal frontal position with regard to the eye and said beamsplitter not affecting the quality of the retinal image and anterior segment;

whereby use of said beamsplitter optimizes the viewing of the anterior segment of the eye by allowing less restrictions on position and size of said imaging device and by providing a frontal viewing of the pupillary area, thereby facilitating and making more precise the moving, maintaining and documenting the size and location of the Maxwellian view illumination of said scanning laser ophthalmoscope in the pupillary area.

6. The method for controlling the Maxwellian view illumination of a scanning laser ophthalmoscope according to claim 4 further including the use of a second infra-red light of a third wavelength for illuminating the anterior segment of the eye, said second infra-red light adjusted in intensity, properly oriented and of such wavelength that no adverse effect is created for observing the retina and for projecting psychophysical stimuli onto the retina with said scanning laser ophthalmoscope;

whereby additional visualization of fiducial landmarks is obtained in the anterior segment of the eye for the localization of the reflection and backscatter of illuminating means of said scanning laser ophthalmoscope.

* * * * *